United States Patent
Moeller-Jensen et al.

(10) Patent No.: US 8,231,589 B2
(45) Date of Patent: *Jul. 31, 2012

(54) IRRIGATION SYSTEM

(75) Inventors: Peter Moeller-Jensen, Hoersholm (DK); Kristoffer Zeuthen, Copenhagen (DK); Jimmy Groetner, Hilleroed (DK); Christian Grünewaldt, Ishoej (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/029,135

(22) Filed: Feb. 17, 2011

(65) Prior Publication Data

US 2011/0184346 A1  Jul. 28, 2011

Related U.S. Application Data

(63) Continuation of application No. 10/520,936, filed as application No. PCT/DK03/00247 on Apr. 11, 2003, now Pat. No. 7,914,505.

(30) Foreign Application Priority Data

Jul. 12, 2002  (DK) .................................. 2002 01096

(51) Int. Cl.
*A61M 31/00* (2006.01)

(52) U.S. Cl. ................... 604/275; 604/99.01; 604/99.02

(58) Field of Classification Search ............... 604/99.01, 604/99.02, 36–39, 43, 93.01, 94.01, 96.01, 604/97.01, 98.01, 98.02, 99.04, 118, 173, 604/327, 334, 911, 257, 258, 275–279; 606/197; 600/156, 158

See application file for complete search history.

(56) References Cited

U.S. PATENT DOCUMENTS

| | | | | |
|---|---|---|---|---|
| 3,889,676 A * | 6/1975 | Greene | .................... | 604/101.05 |
| 4,367,740 A * | 1/1983 | Evanoski, III | .................. | 604/43 |
| 4,386,607 A * | 6/1983 | Miller | .............. | 604/37 |
| 5,368,569 A * | 11/1994 | Sanese | .......... | 604/113 |
| 5,405,319 A * | 4/1995 | Abell et al. | ..................... | 604/27 |
| 6,106,506 A * | 8/2000 | Abell et al. | .................. | 604/275 |
| 6,468,245 B2 * | 10/2002 | Alexandersen | .............. | 604/105 |
| 2003/0073963 A1 * | 4/2003 | Falconer | ...................... | 604/328 |
| 2003/0073971 A1 * | 4/2003 | Saker | ........................... | 604/403 |
| 2003/0073974 A1 * | 4/2003 | Falconer | ...................... | 604/514 |

FOREIGN PATENT DOCUMENTS

DE  585360  * 10/1933

* cited by examiner

*Primary Examiner* — Kevin C Sirmons
*Assistant Examiner* — Laura Schell
(74) *Attorney, Agent, or Firm* — Coloplast Corp., Coloplast A/S; Daniel G. Chapik; Nicholas R. Baumann (57) ABSTRACT

An irrigation system includes a control unit and a pump integrated with the control unit. The control unit includes an adjustment knob attached to a major surface of the control unit, a first conduit extending from a side of the control unit to a reservoir that is configured to contain a volume of irrigation liquid, and a second conduit extending from the side of the control unit to an anal probe that is inflatable for fixation of the anal probe within a user. The adjustment knob has a first setting that is selectable to inflate a cuff of the anal probe and a second setting that is selectable to allow the pump to pump gas into the reservoir and thereby transfer the irrigation liquid from the reservoir through the inflated anal probe.

10 Claims, 6 Drawing Sheets

IRRIGATION SYSTEM

This application is a continuation of U.S. application Ser. No. 10/520,936, filed Dec. 19, 2005, which is now U.S. Pat. No. 7,914,505, which is a nationalization of PCT/DK03/00247 filed Apr. 11, 2003 and published in English.

BACKGROUND OF THE INVENTION

1. Field of the Invention

The present invention relates to an irrigation system comprising a reservoir for irrigating liquid, a probe for arrangement in a user, conduit means for conducting the irrigating fluid from the reservoir to the probe, and a fixation member for fixation of the probe in the user.

2. Description of the Related Art

Disabled persons, such as persons having a spinal cord injury or spina bifida or MS sufferers, with limited limb movement can often not perform their normal bowel function without the need for outside assistance. Examples of such assistance are drugs, digital stimulation, massage or colonic irrigation.

Various bowel irrigation systems are known. One such system is the arrangement disclosed in Applicant's published international application No. WO 98/23312, in which the irrigation medium is fed by gravity from a bag hung from a frame arranged close to the patient. Flow of liquid from the bag to the user is controlled by a flow regulation device operated by the user. As the operation is dependent on gravity, the bag must be positioned at a higher level than the user, and the bag is therefore usually suspended from a frame. This means that the system cannot be readily portable unless the frame can be collapsed for storage.

Portability of equipment is extremely important to disabled persons who are not hospitalised or bed-ridden, if they are to lead as normal a life, as possible and deal with their daily bodily functions. This is particularly important if they travel away from their home.

Bowel care systems are known which are movable on wheels such as those disclosed in U.S. Pat. Nos. 5,019,056 and 4,874,363. These systems comprise a reservoir for the liquid irrigation fluid, a tank for discharged material, a probe for insertion into the patient and ancillary equipment including a pump to pump the irrigation liquid from the reservoir through the pump to the probe. The system is mounted on a carriage with wheels so that it can be moved from one location to another. Although such systems are mobile, they are heavy and cumbersome, and are thus not readily transportable by the user. Consequently, they tend to be restricted to use in hospitals or nursing homes where they can be wheeled from one patient to another. Because of their size and weight, these systems cannot be carried by the users from one place to another and thereby allow them to lead as normal a life as possible.

Furthermore, operating such systems traditionally used often requires full dexterity or even an assisting person.

SUMMARY OF THE INVENTION

With this background it is an object of the present invention to provide an irrigation system that is easy and comfortable to use.

It is a further object of the invention to provide an irrigation system that may readily be transported by the user.

These and further objects are met by means of an irrigation system of the kind mentioned in the introduction, which is characterized in that pumping means are provided for pumping gas into the reservoir to transfer the irrigating liquid from the reservoir to the probe, that the fixation member includes an inflatable cuff, and that the system includes a control unit which may be set in at least a cuff inflating position and a liquid transferring position.

The combination of the pumping means and the incorporation of a control unit that may be set in a number of predetermined operating positions into the irrigation system entails that the user is able to perform the entire irrigation by himself or herself without the need for outside help. Due to the fact that gas is pumped into the reservoir and the irrigating liquid is forced out from the reservoir, it is possible to use a closed system. This entails, i.a., that the closed reservoir may easily be carried and may be placed in any position with respect to the user and not necessarily at a level substantially higher than the user as is the case in the above-mentioned WO 98/23312. Inflation of the cuff and the flow of irrigating liquid are controlled by the control unit, which may be e.g. held by the user or positioned at a place near him or her. The probe is easily inserted with the cuff in its deflated condition, and the inflation of the cuff and the flow of irrigating liquid are controlled by the user in a simple manner by setting the control unit into the appropriate sequential positions. Furthermore, the control unit provides the user with a logical indication of the operational steps to be carried out in order to perform the irrigation.

In an advantageous embodiment, the control unit comprises at least two elements that may be moved with respect to each other into at least said cuff inflating and liquid transferring positions. This provides for a simple and functional design of the control unit.

In an embodiment, which provides for a particularly compact design of the irrigation system, the conduit means includes a first part connecting the control unit with the probe and a second part connecting the reservoir with the control unit, and in which each of said first and second parts comprises a gas conducting tube and an irrigating liquid conducting tube.

The conduit means may include a first part connecting the control unit with the probe and a second part connecting the reservoir with the control unit, and each of said first and second parts may comprise a gas conducting tube and an irrigating liquid conducting tube.

In an embodiment, the conduit means includes an irrigating liquid conducting tube connecting the reservoir with the probe, and at least one gas conducting tube connecting the control unit with the reservoir.

In a preferred embodiment, the control unit may be set in a first position corresponding to an inactive position, a second position corresponding to said liquid transferring position and in which gas is pumped into the reservoir and irrigating liquid is transferred from the reservoir to the probe, and a third position corresponding to said cuff inflating position and in which gas is pumped into the inflatable cuff. By this design, all of the operational steps necessary in order to carry out irrigation, i.e. inflation of the cuff, flow of irrigating liquid and deflation of the cuff are controlled by an appropriate sequential adjustment of the control unit.

It is preferred that when the control unit is set in the inactive position, where the cuff is deflated, then it is not possible to transfer liquid.

Preferably the pumping means is a manually operated pump, such as a bulb or a bellow pump.

The pumping means may also be a powered pump, such as an electrically or pneumatically operated pump, and when used in the above-mentioned preferred embodiment the pump may be deactivated when the control unit is set in the first position and is activated automatically when said control unit is set in the second position.

In one embodiment of the invention the pumping means and the control unit may be in the form of separate units.

In a particularly compact design of the irrigation system, such a pump, whether manually operated or a powered pump, is integrated with the control unit.

Other features and advantages will readily be appreciated from the following description of examples of embodiments.

BRIEF DESCRIPTION OF THE DRAWINGS

In the following the invention will be described in further detail with reference to the schematic drawings, in which FIG. 10 shows a perspective view of a detail of a control unit in a third embodiment of the irrigation system, FIG. 11 shows a sectional view of the detail of the control unit of FIG. 10, along the line XI-XI, FIGS. 12 and 13 show sectional views of the detail of the control unit of FIG. 10, along the lines and XIII-XIII in FIG. 11, and FIGS. 14a to 14c show schematic plan views of the detail of the control unit of FIG. 10 in different operating positions.

DESCRIPTION OF THE PREFERRED EMBODIMENTS

Figure 1A:
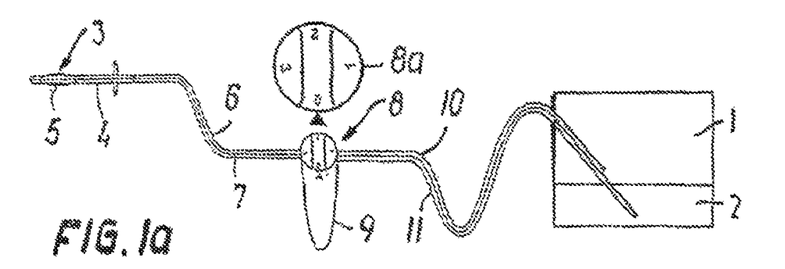
FIGS. 1a to 1e show an irrigation system according to the invention in different operating positions.

In FIG. 1a, an irrigation system is shown in a starting position, in which a reservoir 1 is filled with irrigating liquid 2 to a predetermined level. The irrigating liquid may be any suitable medium such as tap water, isotonic salt water, sterile water or oily substances. The reservoir 1 is formed as a substantially sealed container and is connected with a probe generally designated 3 for arrangement in a user by means of a conduit means in a manner that will be described in further detail in the following.

The probe 3 comprises a shaft portion 4 and a fixation member in the form of an inflatable cuff 5. The inflatable cuff 5 is connected with a tube 6 for conducting an inflating medium to the cuff. This medium may be any suitable fluid, such as gas, e.g. ambient air or any other gas or mixture of gases provided by a pneumatic container, or any liquid, e.g. the same liquid as the irrigating liquid to be described in the following. In this respect, it is noted that the terms "inflate" and "inflatable" etc. should be interpreted as meaning "distend" ear "distensible" by means of any suitable medium. In the following the term "gas conducting tube" will be used. However, as explained in the above this does not exclude that fluids other than gas may be used. The probe 3 is furthermore connected with an irrigating liquid conducting tube 7. In the embodiment shown, the gas conducting tube 6 and the irrigating liquid conducting tube 7 form a first part of the conduit means.

The other end of the first part of the conduit means is connected with a control unit generally designated 8 and comprising an adjustable knob 8a. In the embodiment shown, the control unit is set in different positions by turning the knob and thus at least a part of the control unit with respect to another part or other parts thereof. However, other operating manners are conceivable, such as those involving any displacement of mutually movable parts, e.g. in a series of sliding movements in a combination of sliding and rotational movements. In connection with the control unit 8, pumping means 9 is provided. The control unit 8 is furthermore connected with one end of a second part of the conduit means comprising a gas conducting tube 10 connected with the control unit 8 and the reservoir 1 and an irrigating liquid conducting tube 11. The first and the second part of the conduit means may be provided in the form of separate tubes, but each part may also be incorporated into a single tube having two lumens. Alternatively, only the inflating medium conducting tubes, i.e. in the embodiment shown the gas conducting tubes 6 and 10, are connected with the control unit whereas the irrigating liquid conducting tubes 7 and 11 constitute a single tube connecting the reservoir 1 with the probe 3. This arrangement may e.g. be carried out by means of a two-lumen tube, known per se, of which one lumen is split at the control unit into the two gas conducting tubes leading to and from, respectively, the control unit, whereas the other lumen by-passes the control unit.

Figure 1B:
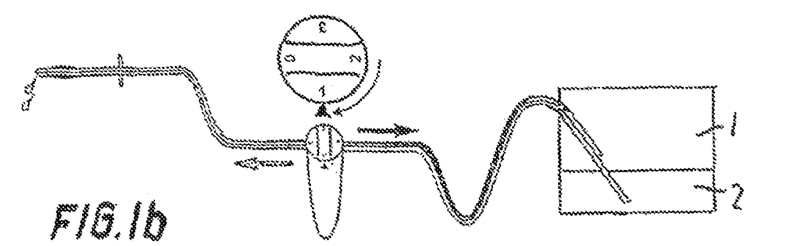

Generally, irrigation is carried out by inflating the cuff in order to secure the probe in position in the user, and subsequently feeding irrigating liquid from the reservoir to the probe. In the irrigation system according to the invention, the following operational steps are carried out:

In the position shown in FIG. 1a, the control unit 8 is in a first or inactive position, indicated by '0' on the knob 8a. By turning the knob 8a to '1', the control unit 8 is brought to a second position, shown in FIG. 1b, in which gas, e.g. air, is pumped through the gas conducting tube 10 into the reservoir 1. As the reservoir is formed as a substantially sealed container, a pressure is built up in the reservoir 1 and irrigating liquid 2 is forced into the conducting tube 11. This step is carried out in order to secure that the liquid conducting tube 7 is emptied of air which would otherwise enter into the bowels of the user and thus cause discomfort to him or her.

Figure 1C:
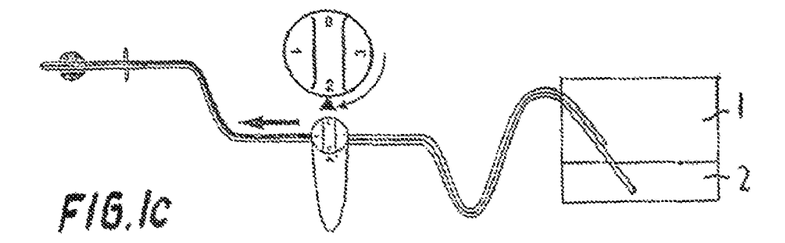
Figure 1D:
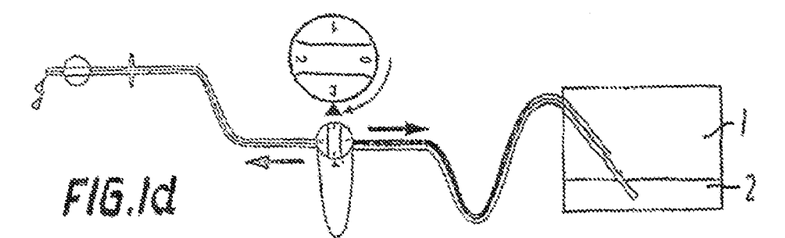
Figure 1E:
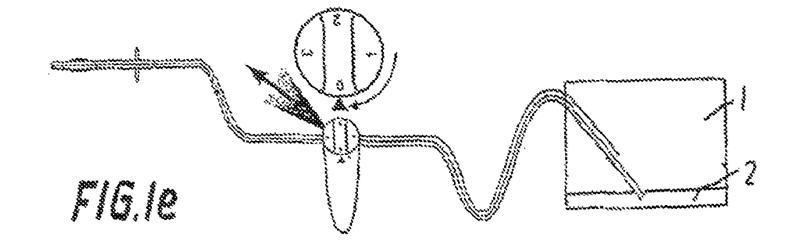

The knob 8a is turned to '2' and the control unit 8 is brought to a third position shown in FIG. 1c. Subsequently, the probe 3 is inserted into the anal opening of the user. When the insertion has been carried out, the cuff 5 is inflated to the desired extent, and the probe 3 is thus secured in the user. In this respect it is noted that the extent to which the cuff is inflated may vary between the individual users, Usually, initial tests are carried out in order to determine the desired extent and during subsequent irrigation procedures, the same amount of inflating medium is lead to the cuff, e.g. by counting the number of compressions in the case of pumping means in the form of a manually compressible bulb.

The control unit 8 is now brought back to its second position, in which gas is pumped to the reservoir 1 and irrigating liquid 2 is pumped to the probe 3. In the embodiment shown in FIG. 1, this operational step is marked as a separate indication on the knob 8a, viz. '3', e.g. in a manner that will be described in connection with FIGS. 2 and 3, below. It is of course conceivable to have only three indications on the knob 8*a* for the first, second and third operating positions.

When irrigation has been completed, e.g. because the reservoir 1 has been emptied of its contents or because the user considers it appropriate, the knob 8*a* is turned to position '0' and the control unit 8 is thus brought back to its first position. Gas present in the system is allowed to escape to the ambience. It is noted that means may be provided in the reservoir in order to secure that gas is prevented from entering the liquid conducting tube leading from the reservoir and possibly further into the user. Such means may e.g. comprise a stop valve containing a floater that follows the surface of the irrigating liquid. Usually, however, a visual inspection of the level of remaining irrigating liquid will be sufficient, possibly in combination with the noise generated by the last of the liquid being forced into the irrigating liquid conducting tube.

In addition to the visual indications on the knob 8*a* in the form of marks '0', the different positions may be indicated by temporary arresting means such as a mechanism comprising a ball and recesses to be engaged by the ball in the different positions.

It is furthermore possible to include one or more back-flow valves into the system in order to ensure that irrigating liquid or contents of the bowels do not flow backwards in the irrigating liquid conducting tube or tubes.

Figure 2A:
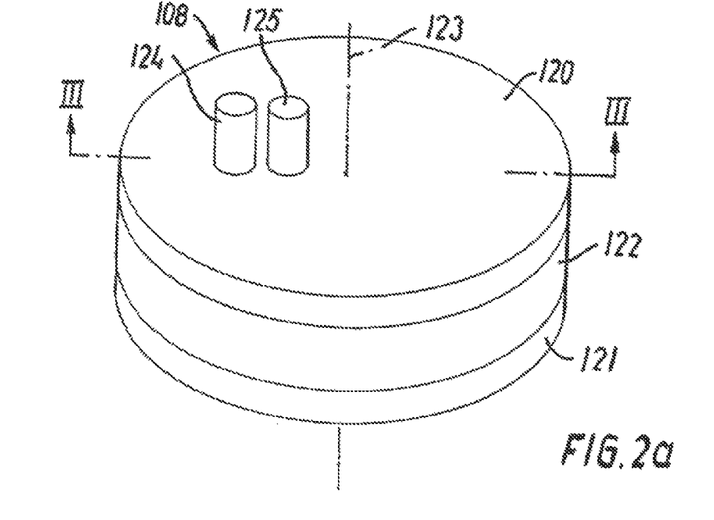
FIG. 2a shows a perspective view of a detail of a control unit in a first embodiment of the irrigation system.
Figure 2B:
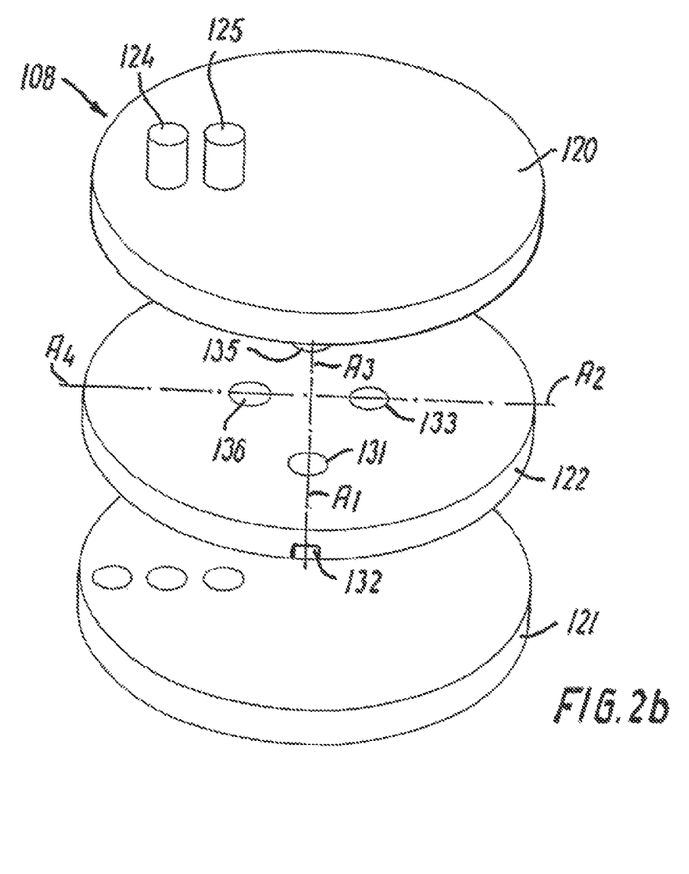
FIG. 2b shows an exploded perspective view of the detail shown in FIG. 2a, FIGS. 3a to 3e show sectional views of the detail of the control unit of FIG. 2, along the line III-III, in different operating positions.
Figure 3A:
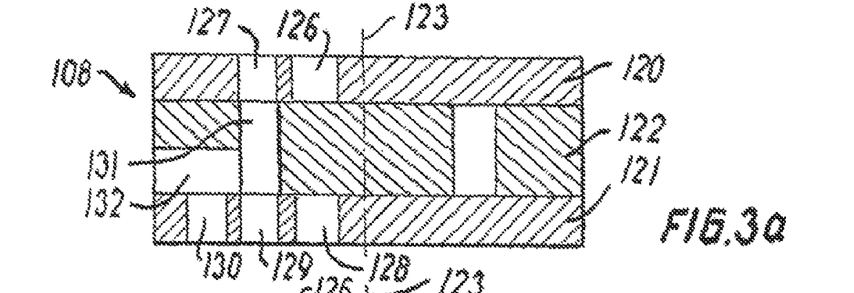
Figures 3B, 3C:
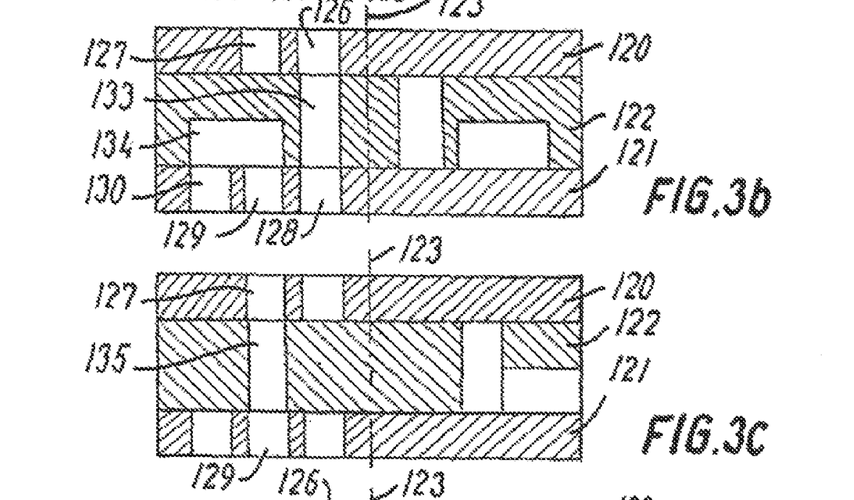
Figures 3D, 3E:
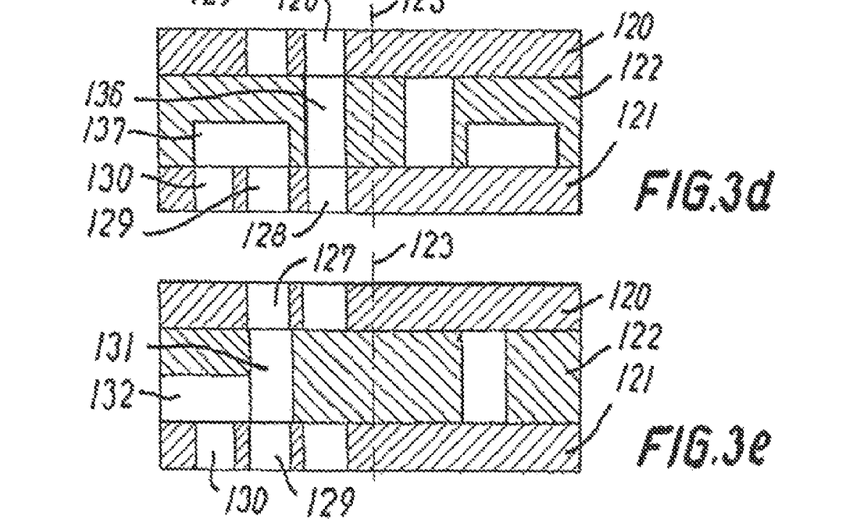

In a first embodiment of the irrigation system, the operational steps described in the above are carried out by means of a control unit 108 shown in FIGS. 2 and 3.

In this embodiment, the control unit 108 comprises a first disc 120, a second disc 121 and an intermediate disc 122 positioned between the first and second discs 120, 121. The intermediate disc 122 is rotatable about an axis of rotation 123 with respect to the first and second discs 120, 121 in any suitable manner, e.g. by means of a shaft extending through all of the discs 120, 121, 122 and engaging drivingly with the intermediate disc 122 only, or with an element extending along at least a part of the periphery of the intermediate disc 122 and engaging drivingly with this disc. The shaft or the element may be connected with a knob as described in the above with respect to FIGS. 1*a* to 1*e*. The first disc 120 is provided with a connecting pipe 124 for connection with the gas conducting tube leading to the inflatable cuff at the probe of the irrigation system, and a connecting pipe 125 for connection with the irrigating liquid conducting tube leading to the probe. As suggested in the above description of FIG. 1, these tubes, which constitute the first part of the conduit means, may be incorporated into a single tube having two lumens.

Correspondingly, the second disc 121 is provided with similar connecting pipes (not shown) for connection with the second part of the conduit means, i.e. the gas conducting tube and the irrigating liquid conducting tube leading to the reservoir of the irrigation system. The second disc is furthermore provided with a connecting pipe (not shown) forming the inlet for gas supplied by the pumping means of the irrigation system.

As shown in FIG. 3, the first disc 120 is provided with a first through-going cavity 126 at a first distance from the axis of rotation 123 and a second through-going cavity 127 at a second distance from the axis of rotation 123, the second distance being larger than the first distance. The first cavity 126 opens into the connecting pipe 125 and is thus in connection with the irrigating liquid conducting tube of the first part of the conduit means connecting the control unit with the probe. The second cavity 127 opens into the connecting pipe 124 and is thus in connection with the gas conducting tube of the first part of the conduit means.

The second disc 121 is provided with a first through-going cavity 128 at the first distance from the axis of rotation 123, a second through-going cavity 129 at the second distance from the axis of rotation 123 and a third through-going cavity 130 at a third distance from the axis of rotation 123, the third distance being larger than the second distance. The first cavity 128 opens into the connecting pipe at the outside of the second disc 121 that is connected with the irrigating liquid conducting tube of the second part of the conduit means leading to the reservoir and the third cavity 130 opens into the connecting pipe that is connected with the gas conducting pipe. The second cavity 129 opens into the connecting pipe connected with the pumping means of the irrigation system.

In the embodiment shown in FIGS. 2*a*, 2*b* and 3*a* to 3*e*, the intermediate disc 122 is provided with a number of through-going cavities and recesses that are distributed as follows:

Along a first line A1 extending from the axis of rotation 123 towards the periphery of the intermediate disc 122, the intermediate disc 122 has a through-going cavity 131 at the second distance from the axis of rotation 123 and an oblong recess 132 extending from the cavity 131 to the periphery of the intermediate disc 122. Along a second line A2 extending at an angle with respect to the first line A1 from the axis of rotation towards the periphery of the intermediate disc, the intermediate disc 122 has a through-going cavity 133 at the first distance from the axis of rotation 123 and an oblong recess 134 opening towards second disc 121 and extending substantially over a distance corresponding to the second and third through-going cavities 129, 130 in the second disc 121. Along a third line A3 extending at angle with respect to the second line from the axis of rotation towards the periphery of the intermediate disc 122, the intermediate disc 122 has a through-going cavity 135 at the second distance from the axis of rotation 123, Along a fourth line A4 extending at an angle with respect to the third line A3 from said axis of rotation 123 towards the periphery of the intermediate disc 122, the intermediate disc 122 has a through-going cavity 136 at the first distance from the axis of rotation and an oblong recess 137 opening towards the second disc and extending substantially over a distance corresponding to the second and third through-going cavities 129,130 in the second disc 121.

It is noted that the cavity and the recess along the above-mentioned fourth line A4 are only necessary in the case, in which the control unit 108 may be set in four discrete positions, as is the case in the embodiment shown in FIGS. 1*a* to 1*e*.

The lines A1-A4 may be distributed uniformly over a revolution, i.e., with a difference of 90° between the lines A1-A4 in the above embodiment, or with any arbitrary angle between the lines.

The operational steps carried out in order to complete irrigation will now be described with reference to FIGS. 3*a* to 3*e*.

FIG. 3*a* indicates an inactive starting position, in which the intermediate disc 122 is set such that the through-going cavity 131 and the oblong recess 132 along the first line A1 are positioned opposite the through-going cavities 126,127 and 128,129,130 of the first and second discs 120,121, such that a through-going passageway for gas is provided at the second distance from the axis of rotation 123, as the cavity 127 of the first disc 120, the cavity 131 of the intermediate disc 122 and the cavity 129 of the second disc 121 are in flush with each other.

In the position shown in FIG. 3*b*, the intermediate disc 122 has been rotated such that the cavity 133 and the recess 134 along the second line A2 are positioned opposite the cavities of the first and second discs. Thus, gas supplied by the pumping means (not shown) into the cavity 129 of the second disc 121 is directed to the reservoir via the recess 134 in the intermediate disc 122, the cavity 130 in the second disc 121 and further on through the gas conducting tube leading from the control unit to the reservoir. As described in the above, the pressure created by the gas supplied to the reservoir causes the irrigating liquid to flow from the reservoir through the irrigating liquid conducting tube leading from the reservoir to the control unit, through the passageway formed by cavities 128, 133 and 126 in the control unit and further through the irrigating liquid conducting tube leading from the control unit to the probe of the irrigation system.

In the position shown in FIG. 3c, the intermediate disc 122 has been turned once again such that the through-going cavity 135 along the third line A3 is positioned opposite the cavities in the first and second discs. In this position, gas supplied from the pumping means is allowed to flow through the passageway formed by cavities 129, 135 and 127 in the control unit and further through the gas conducting tube leading from the control unit to the inflatable cuff, thus inflating the cuff.

When the cuff has been inflated, the intermediate disc 122 is brought to the position in which the cavity 136 and the recess 137 along the fourth line A4 are positioned opposite the cavities in the first and second discs. As explained in the above, this corresponds to the situation shown in FIG. 3b. Thus, gas is allowed to flow from the pumping means to the reservoir, and irrigating liquid is forced from the reservoir through the control unit and further on to the probe, thus performing the irrigation for as long it is possible or desirable.

The irrigation step may be terminated by turning the intermediate disc 122 further or back to its inactive first position, shown in FIGS. 3a and 3e. Gas present in the system, primarily in the inflatable cuff, is allowed to flow off to the ambience through the recess 132. In this respect it is noted that the recess 132 may be replaced by any opening in the intermediate disc, as long as it connects the cavity 131 with the outside of the intermediate disc 122.

The pumping means may be any manually operated pump, such as a resilient bulb, or any pump powered by external means, such as electricity or a pressurized medium.

In case the pump is a powered pump, it may be automatically activated when setting the control unit in its second position, and automatically deactivated in the first position.

As suggested in the embodiment shown in FIGS. 1a to 1e, the pump may be integral with the control unit.

As described in connection with the embodiment of FIGS. 1a-1e it is possible to use a single tube for irrigating liquid leading from the reservoir to the probe. It is also conceivable to inflate the cuff by other media than gas supplied by the pumping means. For instance, the inflating medium may be provided in a separate container, e.g. with a predetermined fluid content. Such a container may be provided with a valve which may be activated in order to deflate the cuff when the irrigation has been completed.

It is furthermore conceivable to design the discs such that the control unit may be set only in a cuff inflating and a liquid transferring position. In this case, ventilation of gas present in the system following irrigation must be carried out in any alternative manner, e.g. in the above suggested solution by a separate vent in the container containing the inflating medium. Alternatively, deflation may be carried out by disconnecting the conducting tube from the control unit and/or the probe.

The cross-section of the through-going cavities may be chosen arbitrarily but is advantageously circular.

In order to provide a substantially sealed transition between the first disc and the intermediate disc and between the intermediate disc and the second disc, at least the intermediate disc is advantageously formed from a resilient material. Alternatively, the first and discs are formed from a resilient material, or all of the discs may be formed from the same, possibly resilient material. The material should possess such a degree of resilience that a satisfying sealing effect is achieved without impeding the movement of the intermediate disc with respect to the first and second discs.

FIGS. 4 to 9 show a control unit 208 of a second embodiment of the irrigation system.

Figure 4:
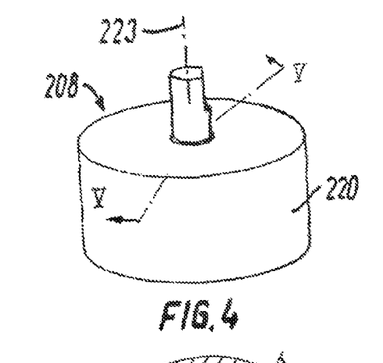
FIG. 4 shows a perspective view of a detail of a control unit in a second embodiment of the irrigation system.
Figure 5:
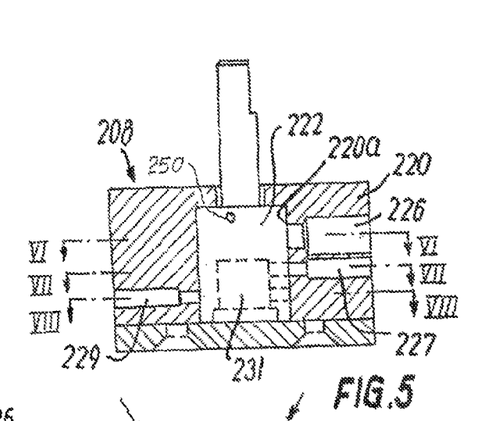
FIG. 5 shows a sectional view of the detail of the control unit of FIG. 4, along the line V-V.
Figure 6:
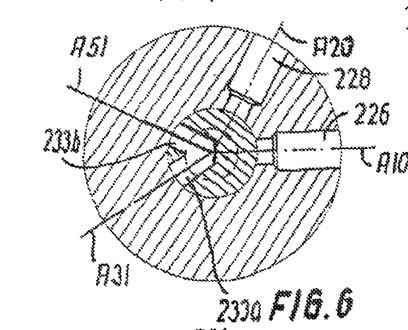
FIGS. 6 to 8 show sectional views of the detail of the control unit of FIG. 4, along the lines VI-VI, VII-VII, VIII-VIII in FIG. 5, FIGS. 9a to 9c show schematic plan views of the detail of the control unit of FIG. 4 in different operating positions.
Figure 7:
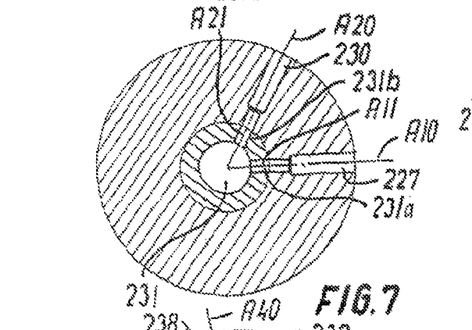
Figure 8:
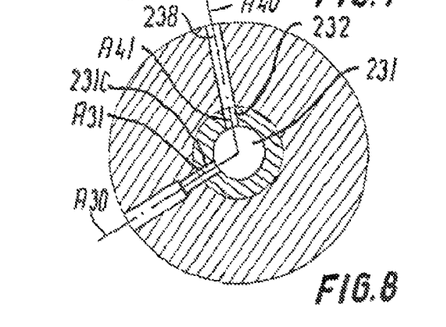

In this embodiment, the control unit 208 comprises an accommodating element 220 and a cylindrical element 222 accommodated in a cylindrical aperture 220a with dimensions corresponding substantially to the outer dimensions of the cylindrical element 222. The cylindrical element 222 is rotatable about an axis of rotation 223 with respect to the accommodating element 220, and the cylindrical element 222 may be set in a number of predetermined operating positions, The first and second part of the conduit means are connected with the accommodating element 220 in a manner that will be described in further detail in the following.

In a first angular position A10, the accommodating element 220 has a first canal 226 in a first height position and a second canal 227 in a second height position. In a second angular position A20, the accommodating element 220 has a third canal 228 in the first height position and a fourth canal 230 in the second height position. In a third angular position A30 the accommodating element has a fifth canal 229 in a third height position, and in a fourth angular position A40 a sixth canal 238 in the third height position. Each canal 226,227,228,230, 229,238 extends from the periphery of the accommodating element 220 to the substantially cylindrical aperture 220a.

In the embodiment shown, the cylindrical element 222 comprises an internal gas distribution compartment 231 having in a first angular position A11 a first passage 231a, in a second angular position A21 a second passage 231b, in a third angular position A31 a third passage 231c and in a fourth angular position A41 a fourth passage 232.

The cylindrical element comprises in the third angular position A31 a first channel 233a extending from substantial the axis of rotation 223 to the periphery of the cylindrical element 222. A second channel 233b extends from substantially the axis of rotation 223 to the periphery of the cylindrical element in a fifth angular position A51 that forms an angle with the third angular position A31 corresponding to the angle between said first and second angular positions A10 and A20 of the accommodating element 220, said first and second channels 223a, 223b being connected with each other at the axis of rotation 223.

The first canal 226 is connected with the irrigating liquid conducting tube and the second canal 227 with the gas conducting tube of the first part of the conduit means, i.e. the part leading to the probe. The third canal 228 is connected with the irrigating liquid conducting tube and the fourth canal 230 with the gas conducting tube of the second part of the conduit means, i.e. the part leading to the reservoir. The fifth canal 229 is connected with the pumping means of the irrigation system, and the sixth canal 238 is connected with the ambience.

Alternatively, the fifth canal may be positioned such that the internal gas distribution compartment is supplied with gas from the pumping means independently of the movement of the cylindrical element with respect to the accommodating element. This may, e.g. be carried out by extending the compartment with a portion below the cylindrical element and leading the gas to this portion of the compartment. This eliminates the risk that the cylindrical element is inadvertently turned into a position, in which the cuff is deflated before irrigation has been completed.

Furthermore, sealing means known per se may be provided between at least the first and second heights such that the liquid conducting passageways are sealed with the gas conducting passageways, and between the liquid conducting passageways and the exterior the control unit.

The operational steps carried out in order to complete irrigation will now be described with reference to FIGS. 9a to 9c.

Figure 9A:
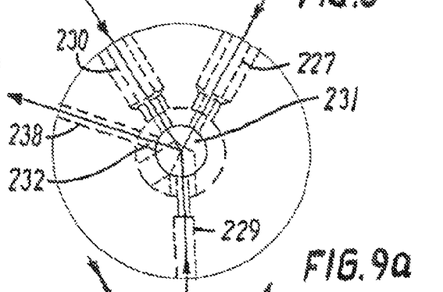

In FIG. 9a, the cylindrical element 222 is in its first position, in which the first angular positions A11 and A10 of the cylindrical element 222 and the accommodating element 220, respectively, substantially coincide with each other. The second angular positions A21 and A20, the third angular positions A31 and A30, and the fourth angular position A41 and A40 coincide as well. Gas present in the irrigation system is thus allowed to flow off to the ambience through the fourth passage 232 and the sixth canal 238, the internal gas distribution compartment 231 thus being in connection with the probe via the second canal 227, the reservoir via the fourth canal 230 and the pumping means via the fifth canal 229 in addition to the sixth canal 238 and thus with the ambience.

Figure 9B:
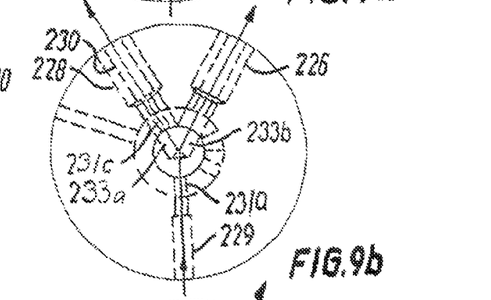

By turning the cylindrical element 222 in the clockwise direction to the position shown in FIG. 9b, gas supplied from the pumping means flows into the internal gas distribution compartment via the fifth canal 229 and the first passage 231a and further on through the third passage 231c into the reservoir. Irrigating liquid is forced from the reservoir back into the control unit 208. As the channels 233a and 233b of the cylindrical element 222 are positioned opposite the third and first canals 228 and 226, respectively, in the accommodating element 220, a passageway for irrigating liquid is formed in the control unit 208, and irrigating liquid is thus allowed to flow off from the first canal 226 to the irrigating liquid conducting tube and further on to the probe.

Figure 9C:
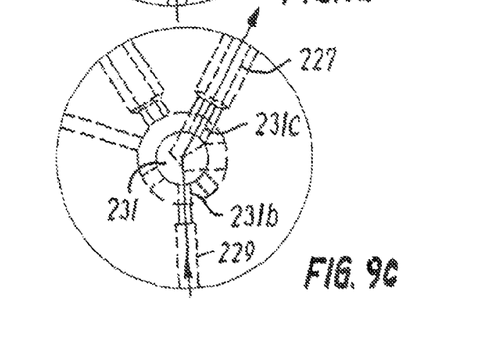

In the third position shown in FIG. 9c, gas is allowed to flow from the pumping means to the internal gas distribution compartment 231 through the fifth canal 229 and the second passage 231b, and from the compartment 231 via the third passage 231c and the second canal 227 further on to the inflatable cuff.

The cylindrical element is then turned back into the second position and irrigation is carried out for as long as desired. By turning the cylindrical element back into the first position shown in FIG. 9a, the cuff may be deflated and the probe removed from the user.

As suggested in connection with the embodiment of FIGS. 1a-1c the control unit may comprise arresting means for arresting the cylindrical element temporarily in the different positions. In the embodiment shown, the accommodating element comprises a ball (not shown) displaceable in the radial direction and a number of recesses corresponding to the first, second and third positions, of which one recess 250 is shown in FIG. 5.

As described in the above in connection with the embodiment of FIGS. 2 and 3, the first and second parts of the conduit means may be formed as single tubes with two lumens, or as separate tubes, whereby it is possible to position the canals in the accommodating element differently from the positions shown in FIGS. 4 to 9. Likewise it is possible to let the irrigating liquid conducting tube by-pass the control unit and to have a separate container for supplying the inflating medium.

It is furthermore conceivable to design the control unit 208 such that the cylindrical element may be set in the cuff inflating and liquid transferring positions only.

In FIGS. 10 to 14, an alternative embodiment to the embodiment shown in FIGS. 4 to 9 is illustrated. Elements having the same or analogous function have the same reference numerals with '100' added to them.

Figures 10, 11, 12, 13, 14A, 14B, 14C:
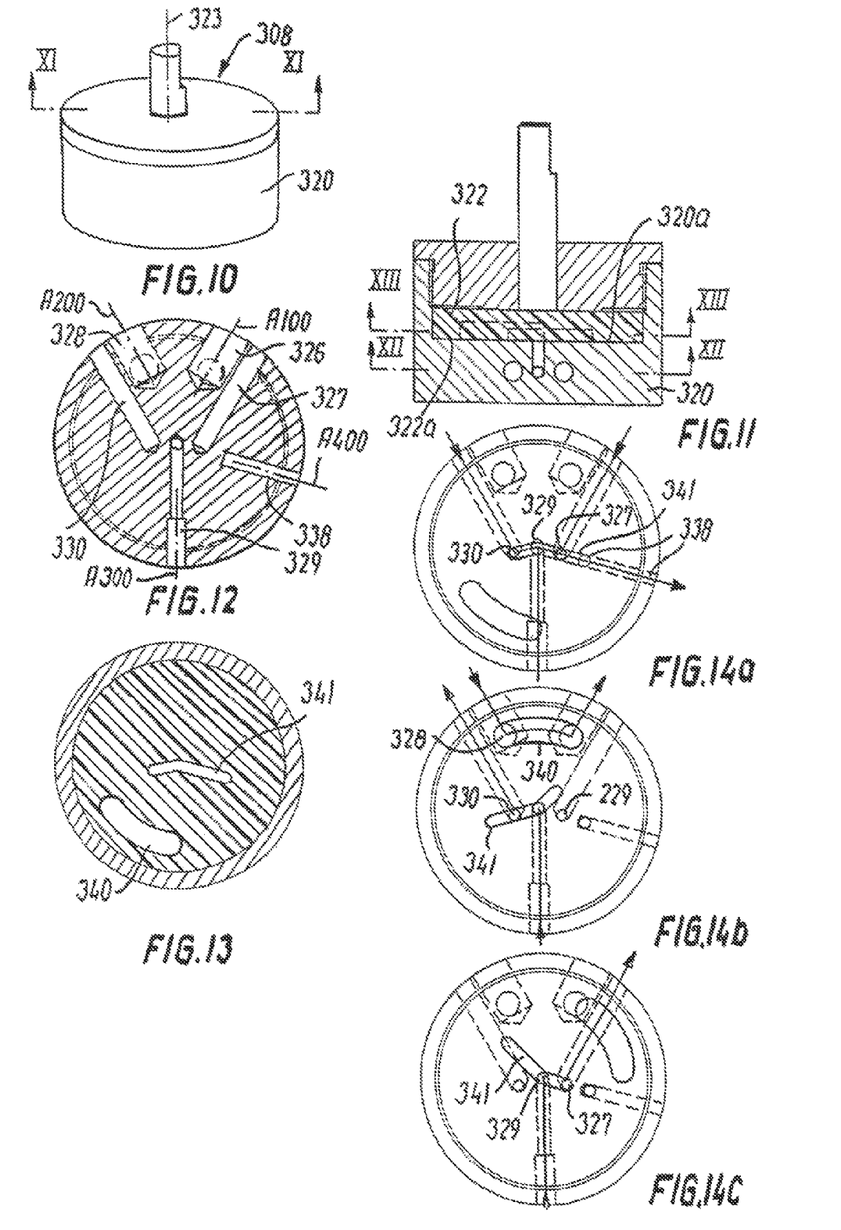

In this embodiment the accommodating element 320 comprises an abutment face 320a for a bottom face 322a of the cylindrical element 322. As in the above embodiment, the cylindrical element 322 is rotatable with respect to the accommodating element 320 about the axis of rotation 323.

In a first angular position A100 the accommodating element 320 has a first canal 326, and in a second angular position A200 a third canal 328. Each of the first and third canals 326, 328 extends from the periphery of the accommodating element 320 in a direction towards the axis of rotation 323 to a predetermined position and from said predetermined position to the abutment face 320a. Along a line substantially parallel with a line extending through said first angular position A100, the accommodating element 320 has a second canal 327, and along a line substantially parallel with a line extending through the second angular position A200 a fourth canal 330. Each of the second and fourth canals 327, 330 extends from the periphery of the accommodating element 320 to a predetermined position and from said predetermined position to the abutment face 320a. In a third angular position A300 the accommodating element 320 has a fifth canal 329 extending from the periphery of the accommodating element to the axis of rotation 323 and further on to the abutment face 320a, and in a fourth angular position A400 a sixth canal 338 extending from the periphery of the accommodating element towards the axis of rotation to a predetermined position and from that position to the abutment face 320a.

In the bottom face 322a the cylindrical element 322 has a first oblong recess 340 opening towards the abutment face 320a and having an extent corresponding substantially to the distance between the first and third canals 326 and 328 of the accommodating element 320, and a second oblong recess 341 opening towards the abutment face 320a and having such a configuration that it extends, in a first position, from the fourth canal 330 through the fifth canal 329 and the second canal 327 to the sixth canal 338.

In the embodiment shown, the first oblong recess 340 has a substantially curved shape.

The first canal 326 is connected with the irrigating liquid conducting tube and the second canal 327 with the gas conducting tube of the first part of the conduit means, the third canal 328 is connected with the irrigating liquid conducting tube and the fourth canal 330 with the gas conducting tube of the second part of the conduit means. The fifth canal 329 is connected with the pumping means, and the sixth canal 338 is connected with the ambience.

The operational steps carried out in order to complete irrigation will now be described with reference to FIGS. 14a to 14c.

In the first position shown in FIG. 14a the second recess 341 provides connection between the second, fourth, fifth and sixth canals as described in the above, gas present in the irrigation system is allowed to flow off to the ambience through the sixth canal 338.

By turning the cylindrical element 322 in the clockwise direction to the position shown in FIG. 14b, the first recess 340 is moved into a position, in which it covers the first and third canals 326, 328, and the second recess 341 is moved into a position, in which it covers the fourth and fifth canals 330, 329 only. Gas supplied from the pumping means flows through the fifth canal 329 and out through the fourth canal 330 via the second recess 341 and further on through the gas conducting tube of the second part of the conduit means and into the reservoir. As described in connection with the above embodiments, irrigating liquid is forced from the reservoir into the control unit 308. As the first recess 340 provides a passageway, irrigating liquid is able to flow on to the probe through the irrigating liquid conducting means of the first part of the conduit means.

In the third position shown in FIG. 14c, the second recess 341 has been moved into a position in which it covers the second and fifth canals 327, 329 only. Consequently, gas may flow from the pumping means through the control unit and into the inflatable cuff via the gas conducting tube of the first part of the conduit means leading to the probe of the irrigation system.

The cylindrical element 322 is then turned back into the second position and irrigation is carried out for as long as desired. By turning the cylindrical element 322 back into the first position shown in FIG. 14a, the cuff relay be deflated and the probe removed from the user.

In case the first and second parts of the conduit means are not formed as single tubes with two lumens, it is possible to position the canals in the accommodating element differently from the positions shown in FIGS. 10 to 14.

It is furthermore conceivable to design the control unit 308 such that the cylindrical element y be set in the cuff inflating and liquid transferring positions only.

Figure 15:
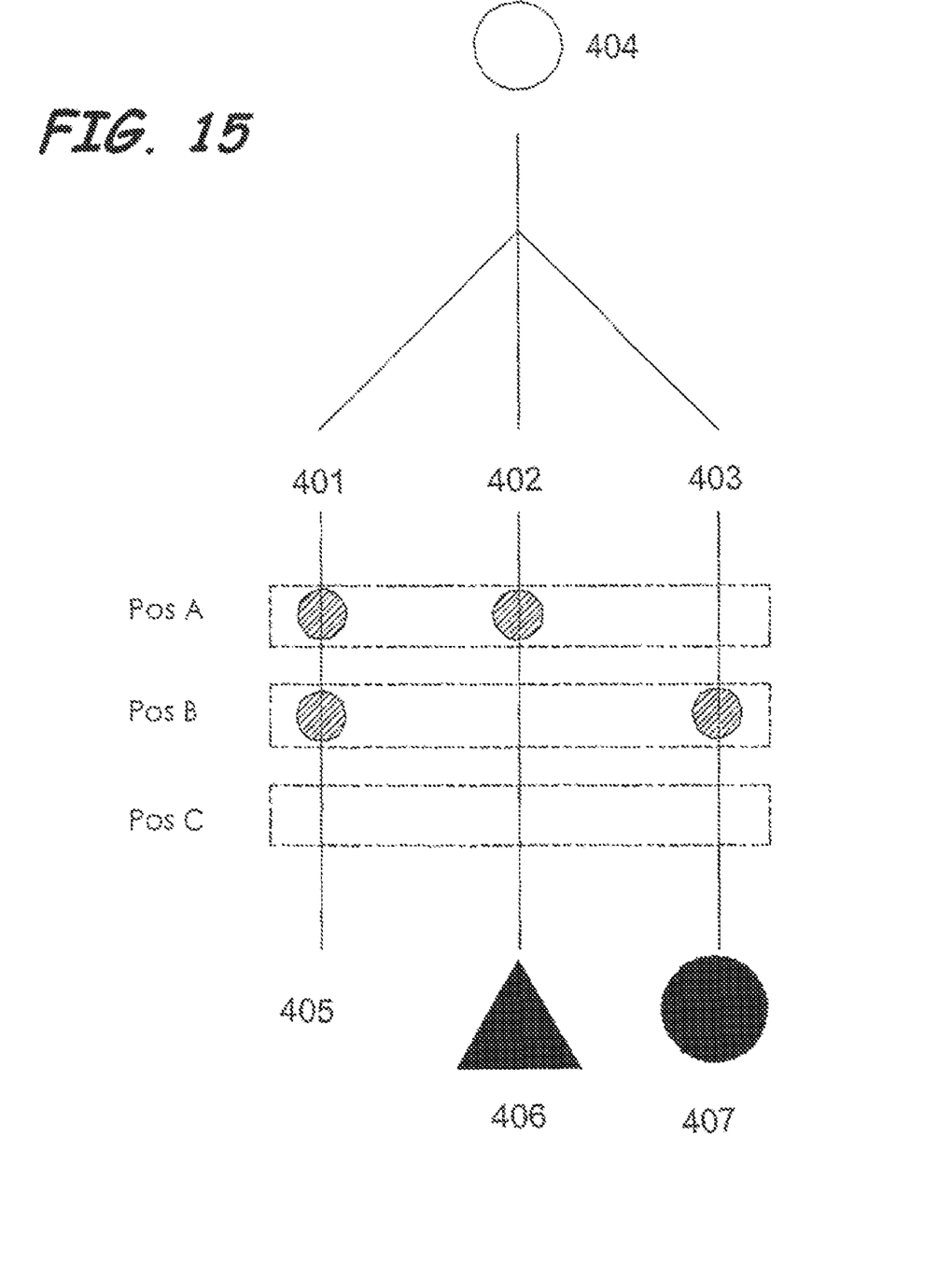
FIG. 15 shows the principles of one embodiment of the invention.

In a preferred embodiment of the invention the control unit is elaborated on peristaltic principles. The principle of the control unit is shown in FIG. 15. The unit comprises three flexible tubes, 401, 402 and 403, e.g. silicone tubes. The tubes are connected in one end to a pump 404. The first tube 401 serves as gas outlet 405, the second tube 402 supplies gas to a fluid reservoir 406 and the third tube 403 supplies gas to an inflatable cuff 407, said cuff being a part of a probe. A separate tube (not shown) from the fluid reservoir transports the fluid from the reservoir to the probe. The three tubes 401, 402, 403 may be individually compressed by compressing means, such as a roller or a plunger, in such a way that no gas or fluid is allowed to pass through the tube.

The compression means may be operated into three positions: Position A, the cuff inflating position, where tube 401 and 402 are compressed, enabling gas to pass through tube 403 in order to inflate the cuff 407, Position B, the liquid transferring position, where tube 401 and tube 403 are compressed, enabling gas to pass through tube 402 into the fluid reservoir 406, whereby the reservoir is pressurised and the fluid may be displaced from the reservoir to the probe by the separate tube, and Position C, the inactive position, where none of the tubes are compressed, relieving the pressure of both the cuff and the reservoir. In position C, the cuff 407 is deflated and the pressure is also relieved from the fluid reservoir 406, thus stopping the flow of liquid to the probe. It is preferred that both the pressure on the inflatable cuff and the pressure on the fluid reservoir are relieved at the same time (Position C), as a deflation of the cuff while liquid still is flowing from the reservoir to the probe may cause a messy and highly undesirable situation for the user.

The above describes peristaltic principle may also be used with two tubes, for the cuff inflating position and the liquid transferring position. In this case the gas outlet may be in the form of a separate valve.

The peristaltic principle is advantageous to use in the control unit of the invention as the liquid and gas of the system are contained in a closed system of tubes, being opened or closed by compression of the tube. A system being less vulnerable, to leakage, and inaccuracies is achieved.

The invention should not be regarded as being limited to the embodiments described in the above but various modifications of and combinations between the various embodiments may be carried out without departing from the scope of the following claims.

For instance, the control unit may comprise activating and deactivating means for electronic control of pumping means in the form of e.g. a number of pumps distributed in the irrigation system.

Furthermore, the irrigation system may be used for dispensing any fluid, such as e.g. fluids introduced into the body with a view to radiological examination.

What is claimed is:

1. An irrigation system comprising:
a control unit and a pump integrated with the control unit, the control unit including an adjustment knob attached to a major surface of the control unit, a first conduit extending from a side of the control unit to a reservoir that is configured to contain a volume of irrigation liquid, and a second conduit extending from the side of the control unit to an anal probe that is inflatable for fixation of the anal probe within a user;
wherein the adjustment knob has a first setting that is selectable to inflate a cuff of the anal probe and a second setting that is selectable to allow the pump to pump gas into the reservoir and thereby transfer the irrigation liquid from the reservoir through the inflated anal probe.

2. The irrigation system of claim 1, wherein the pump is integrated with the side of the control unit.

3. The irrigation system of claim 1, wherein the pump is a powered pump.

4. The irrigation system of claim 1, wherein the pump is a manual pump.

5. The irrigation system of claim 1, wherein the reservoir is a sealed reservoir such that pumping gas into the reservoir in the second setting displaces the irrigation liquid from the reservoir and forces the irrigation liquid through the inflated anal probe.

6. The irrigation system of claim 1, wherein the adjustment knob of the control unit is movable between a cuff inflating position and a liquid transferring position, and the control unit includes movable elements including a first disc connected with the second conduit and a second disc connected with the first conduit, wherein positions of the first disc and the second disc are independently adjustable through movement of the adjustment knob.

7. The irrigation system of claim 6, wherein the first disc includes a first through-going cavity and the second disc includes a second through-going cavity, and positions of the first and second through-going cavities are independently adjustable by movement of the adjustment knob.

8. The irrigation system of claim 1, wherein the second conduit includes a first part connecting the control unit with the anal probe and a second part connecting the reservoir with the control unit, each of said first and second parts including a gas conducting tube and an irrigating liquid conducting tube.

9. An anal irrigation system comprising:
a reservoir that is sized to contain a volume of irrigation liquid;
an anal probe that is inflatable for fixation within an anal opening of a user; and
a pump integrally formed with a control unit, the control unit including a perimeter formed by a side surface and a major surface connected to the perimeter, an adjustment knob attached to the major surface of the control unit, a first conduit extending from the side surface of the control unit to the reservoir, and a second conduit extending from the side surface of the control unit to the anal probe;

wherein the adjustment knob has a first setting that is selectable to inflate a cuff of the anal probe and a second setting that is selectable to allow the pump to pump gas into the reservoir and thereby transfer the irrigation liquid from the reservoir through the inflated anal probe.

10. The anal irrigation system of claim 9, wherein the pump is integrally formed on the side surface of the control unit.

* * * * *